United States Patent
Doerr et al.

(10) Patent No.: US 8,423,205 B2
(45) Date of Patent: Apr. 16, 2013

(54) CONTROL DEVICE FOR COMMUNICATION WITH A MEDICAL IMPLANT AND A MACHINE

(75) Inventors: Thomas Doerr, Berlin (DE); Michael Diebold, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 149 days.

(21) Appl. No.: 13/070,411

(22) Filed: Mar. 23, 2011

(65) Prior Publication Data

US 2011/0257814 A1    Oct. 20, 2011

(51) Int. Cl.
*G06F 17/00* (2006.01)
*G06F 19/00* (2006.01)
*G06F 21/00* (2006.01)
*A61N 1/00* (2006.01)

(52) U.S. Cl.
USPC ........ 701/2; 607/60; 607/32; 701/36; 701/70; 701/1; 701/45; 701/63; 705/50; 705/2; 705/3

(58) Field of Classification Search .................. None
See application file for complete search history.

(56) References Cited

U.S. PATENT DOCUMENTS

| | | | |
|---|---|---|---|
| 6,480,744 B2 | 11/2002 | Ferek-Petric | |
| 2002/0099424 A1 | 7/2002 | Ferek-Petric | |
| 2002/0169482 A1 | 11/2002 | Servaas | |
| 2007/0135855 A1 | 6/2007 | Foshee et al. | |
| 2008/0097912 A1* | 4/2008 | Dicks et al. | 705/50 |

FOREIGN PATENT DOCUMENTS

| | | |
|---|---|---|
| EP | 2026229 | 2/2009 |
| WO | WO 2004/024230 | 3/2004 |

OTHER PUBLICATIONS

European Search Report dated Aug. 5, 2011 (8 pages).

* cited by examiner

*Primary Examiner* — Thomas Tarcza
*Assistant Examiner* — Garrett Evans
(74) *Attorney, Agent, or Firm* — ARC IP Law, PC; Joseph J. Mayo (57) ABSTRACT

A safety system comprising an implant, a control device, and a machine. The machine has a control unit which is designed to allow operation of the machine only when a unique identifier has been received, and to set an operating mode of the machine as a function of the received suitability index. The implant is designed to detect physiological data of an implant wearer, and to either generate a suitability index based on detected physiological data and transmit the suitability index to the control device, or to transmit the physiological data itself to the control device.

15 Claims, 8 Drawing Sheets

CONTROL DEVICE FOR COMMUNICATION WITH A MEDICAL IMPLANT AND A MACHINE

This application claims the benefit of U.S. Provisional Patent Application 61/325,826, filed 20 Apr. 2010, the specification of which is hereby incorporated herein by reference.

BACKGROUND OF THE INVENTION

1. Field of the Invention

Embodiments of the invention relate to a control device that on the one hand is able to receive, and which on the other hand is able to transmit data associated with the received data to a machine control system.

2. Description of the Related Art

From U.S. Pat. No. 6,480,744 B2, it is known that, for example, the fitness of the wearer of an implant such as a cardiac pacemaker, for example, to drive may be limited under certain conditions which are to be detected by the implant, and it is therefore desirable that a vehicle, as a machine which is operated by an implant wearer with limited fitness to drive, automatically performs differently, depending on the degree of limitation of the fitness to drive. Thus, it is proposed in U.S. Pat. No. 6,480,744, for example, that a vehicle control system as a machine control system brakes or stops a vehicle before or during the time that the medical implant delivers a treatment, for example a defibrillation shock. For this purpose, the implant has previously detected, for example, a defibrillation of the heart of the implant wearer which requires treatment. U.S. Pat. No. 6,480,744 describes the direct influencing of the vehicle control system by the medical implant.

BRIEF SUMMARY OF THE INVENTION

One or more embodiments of the invention relate to a control device that on the one hand is able to receive data from a medical implant, and which on the other hand is able to transmit data associated with the received data to a machine control system in order to influence the performance of the machine, and in particular the response of the machine to the control actions of a user.

The control device according to embodiments of the invention prevents such direct influencing of the vehicle control system as a machine control system by the fact that the control device is connected as a relay station between an implant and a particular machine control system and is able to communicate wirelessly with both, so that the connection between the implant and the machine or vehicle control system is indirect.

According to the invention, for this purpose the control device has a first interface for wireless communication with an implant, and a second interface for communication with a machine control system, as well as a memory for a unique identifier. The first interface is designed to receive from an implant physiological data or a suitability index which describes the fitness of an implant wearer to operate a machine. The second interface is designed to transmit the suitability index together with the unique identifier to a particular machine control system of a particular machine.

The control device is thus used on the one hand as a type of key having as a component the unique identifier which is necessary for completely or partially activating the machine control system. On the other hand, the control device is used as a relay station for transmitting a suitability index to the machine control system, this suitability index being derived from physiological parameters detected by the implant or from physiological data derived therefrom which describe physiological states. For this purpose, the physiological data are classified, using a classification unit, and associated with different degrees of fitness. The suitability index describes a particular degree of fitness. The classification unit may, for example, be a component of the control device, or alternatively may be a component of the implant. In the first case the implant transmits physiological data to the control device, and these physiological data are assigned to different degrees of fitness by the classification unit in the control device, thus generating a corresponding suitability index. Alternatively, the association of physiological data with degrees of fitness and the generation of corresponding suitability indices may take place in the implant itself. In that case, the implant already transmits a particular suitability index to the control device, and the control device as a relay station relays this suitability index together with the unique identifier to a particular machine control system.

The advantage realized by using the control device according to one or more embodiments of the invention is that, in contrast to the prior art, the medical implant and a particular machine, for example a vehicle, to be operated by the implant wearer need not, and cannot, communicate directly with one another. This allows, for example, the control device to be used as a key independently from an implant. In this case the control device transmits only the unique identifier, and the machine is able to perform in the manner of, for example, a conventional vehicle whose vehicle control system as a machine control system performs in the manner of conventional vehicle control systems which are not designed to respond differently to different degrees of driving fitness. By the association of the control device with an implant on the one hand and with a machine, in particular a vehicle, on the other hand it is easily ensured that a particular implant wearer is in fact the driver of a corresponding vehicle (i.e., the operator of a corresponding machine) and not a passenger, for example, provided that only the implant wearer himself uses his own control device as a vehicle key.

In a first particularly preferred design variant the control device is designed as a machine key, in particular as a vehicle key, and for this purpose has a corresponding transponder for transmitting the unique identifier. The second wireless interface on the machine side is designed to operate in the Medical Data Service (MEDS) frequency range of 401-402 MHz and 405-406 MHz and in the Industrial, Scientific and Medical (ISM) frequency range of 433 MHz and 2.4 GHz.

The first wireless interface preferably has a receiver which operates in the Medical Implant Communication Service (MICS) frequency range. This frequency range lies in the frequency band between 402 and 405 MHz, and is reserved for wireless communication with medical implants.

A likewise particularly advantageous continuation of the basic concept is that the control device contains a classification unit which is designed to assign data received from an implant regarding the physiological state of a patient to one or more suitability classes, and to generate a corresponding suitability index which the control device is then able to transmit via the second interface to an appropriate control system of a machine. The advantage of this approach is that the classification unit on the one hand may be specifically tailored to the special physiological concerns of a particular patient, and on the other hand may be adapted to requirements to be imposed for fitness to operate a particular machine. For example, unrestricted fitness to drive a vehicle is indicated only when a patient's capacity for perception and responsiveness are uninterrupted.

According to one or more embodiments of the invention, a safety system is also proposed which comprises an implant, a control device of the type described above, and a machine, the machine having a control unit which is designed to allow operation of the machine only when a unique identifier has been received, and to set an operating mode of the machine as a function of the received suitability index. The implant is designed to detect physiological data of an implant wearer, and to either generate a suitability index based on detected physiological data and transmit the suitability index to the control device, or to transmit the physiological data itself to the control device.

According to one or more embodiments of the invention, an implant-control device combination is also proposed which comprises a medical implant and a control device of the type described herein, the implant being designed to detect physiological data of an implant wearer and to transmit the physiological data to the control device, and the control device having a classification unit which is designed to receive physiological data, in each case to assign received physiological data to one of a plurality of specified suitability classes, and to generate a suitability index which denotes the particular assigned suitability class and to provide the suitability index to the second interface. In this variant the classification is thus made by the control device. This has the advantage that the classification of fitness is based precisely on the particular machine, for example a vehicle, associated with the particular control device.

According to one alternative implant-control device combination having a medical implant and a control device of the type described herein, the implant is designed to detect physiological data of an implant wearer, and the implant has a classification unit which is designed to receive physiological data, assign each particular physiological data item to one of a plurality of specified suitability classes, and to generate a suitability index which denotes the particular assigned suitability class and to transmit the suitability index to the control device, the control device being designed to provide a particular suitability index, received from the implant, to the second interface of the control device. In this case the assignment of the physiological data to different suitability classes may be better tailored to the particular implant wearer.

The implant is preferably a cardiac stimulator such as a cardiac pacemaker or cardioverter/defibrillator, for example. Alternatively, the implant may be strictly a monitoring implant without an independent therapeutic function.

A further aspect of the invention is a method for controlling a machine, comprising the following steps:
  Generating physiological parameters which describe physiological data by use of an implant,
  Forming a suitability index from the physiological data, and
  Transmitting the suitability index together with a unique identifier to a machine control system.

BRIEF DESCRIPTION OF THE DRAWINGS

One or more embodiments of the invention is described in greater detail on the basis of exemplary embodiments, with reference to the figures, which show the following.

DETAILED DESCRIPTION OF THE INVENTION

Figure 1:
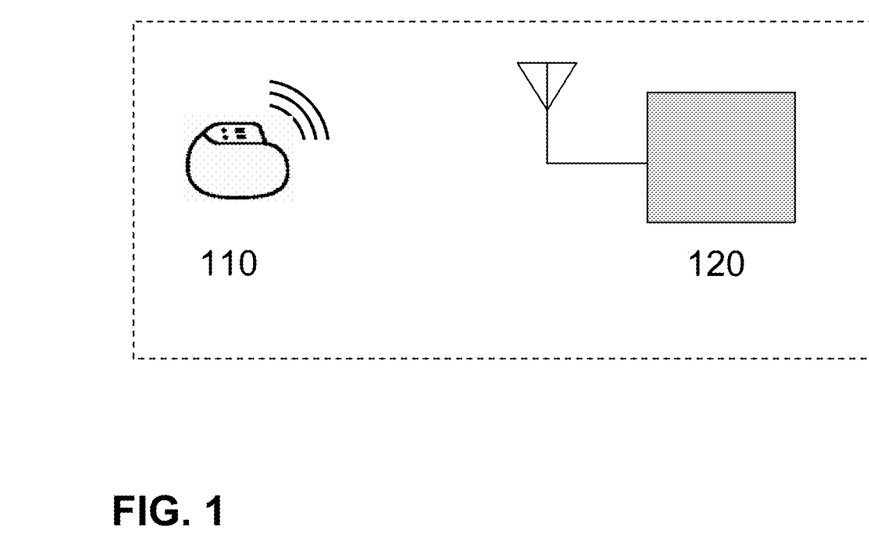
FIG. 1 is an illustration of the prior art.

FIG. 1 illustrates the prior art described in the above-referenced patent. In this case the implant communicates directly with the components of the vehicle system. An electronic implant 110 contains a transmitter, and a vehicle 120 contains a receiver. In this system, no distinction is made concerning whether the wearer of the implant 110 is moved in the vehicle as the driver or the passenger. Thus, it would be possible for the driver assistant system to be unintentionally or erroneously influenced by the implant of a passenger. Furthermore, the entire vehicle must also meet the requirements for a medical product system with regard to development, registration, and product life cycle. Nonreactive operation of the electronic implant is very difficult to achieve when the vehicle system malfunctions.

Figure 2:
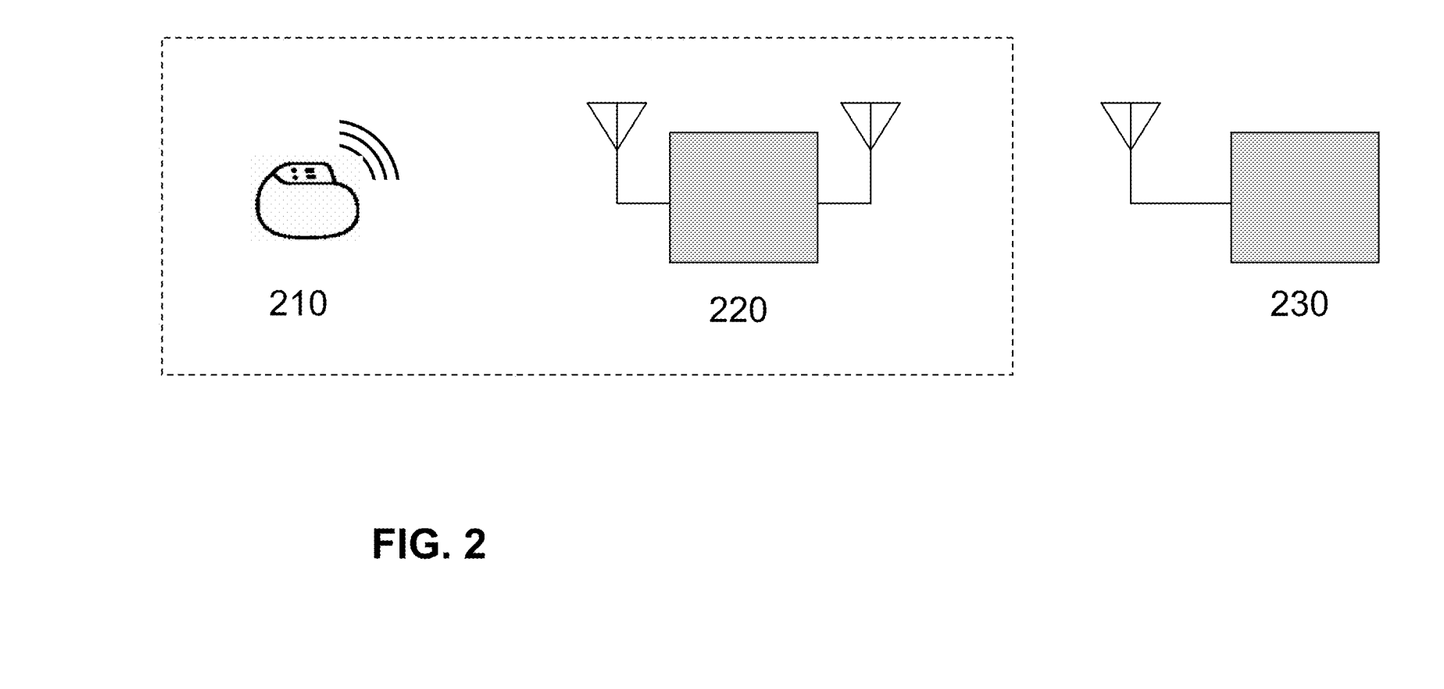
FIG. 2 is an illustration of a safe implant-vehicle communication according to the invention.

FIG. 2 illustrates the implementation according to one or more embodiments of the invention of a safe implant-vehicle communication. In this case the electronic implant 210 communicates bidirectionally, in a band preferred for the implant communication (MICS or ISM), with a control device 220 which at the same time constitutes a vehicle key. The vehicle key 220 always simultaneously functions as a relay station for a vehicle 230 when the vehicle has been started with this key 220. The vehicle key 220 (i.e., the control device), as a relay station for the communication with the implant 210, contains the necessary safety devices, for example a firewall, to ensure operation of the implant which is nonreactive to malfunctions of the vehicle. The communication between the vehicle key 220 and the vehicle 230 takes place on a second communication channel which is basically independent of the implant communication.

In this implementation according to the invention, it is necessary to classify only the electronic implant and the relay station as medical products.

Figure 3:
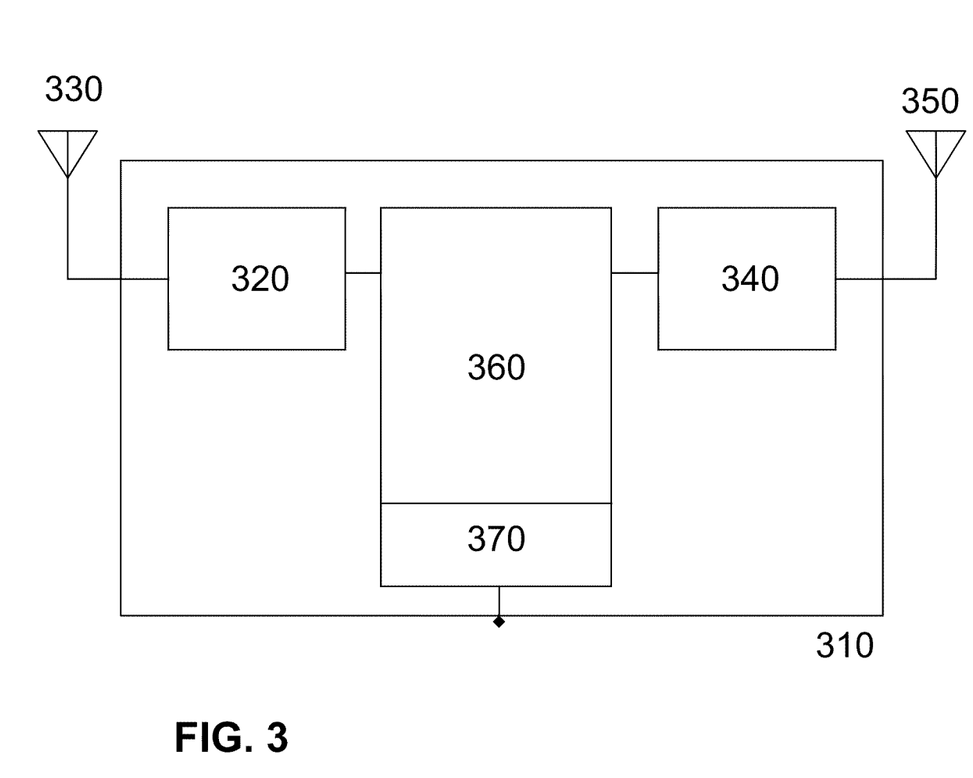
FIG. 3 shows a control device according to the invention as a nonreactive relay station.

FIG. 3 illustrates an implementation of the nonreactive communication with the vehicle. The control device 310 illustrated here is designed as a relay station, and has a first communication module 320 which operates in the MICS band, for example, and which is connected to a first antenna 330. This communication unit is used solely for communication between the electronic implant and the relay station.

The control device 310 also includes a second communication module 340 which operates in the ISM or MEDS band, for example, and which is configured with a corresponding antenna 350 for communication with the vehicle electronics system. The ISM band is currently already used in the vehicle for access control (Keyless Go).

A security server 360 ensures that the implant communication is independent from the vehicle communication. This security server 360 may be designed as a simple command interpreter or as a relatively complex firewall, and has an interface 370 which allows maintenance of the security server in the medical product system.

The illustrated relay station may be implemented either as a mobile device associated with the patient or as a system installed in the vehicle. In the design in the vehicle, this unit is installed in such a way that it may be easily removed by the medical product manufacturer for maintenance purposes so that the maintenance interface 370 is accessible. On the other hand, the maintenance interface 370 is not accessible for vehicle maintenance, thus basically ruling out a reaction as the result of measures of vehicle maintenance.

Figure 4:
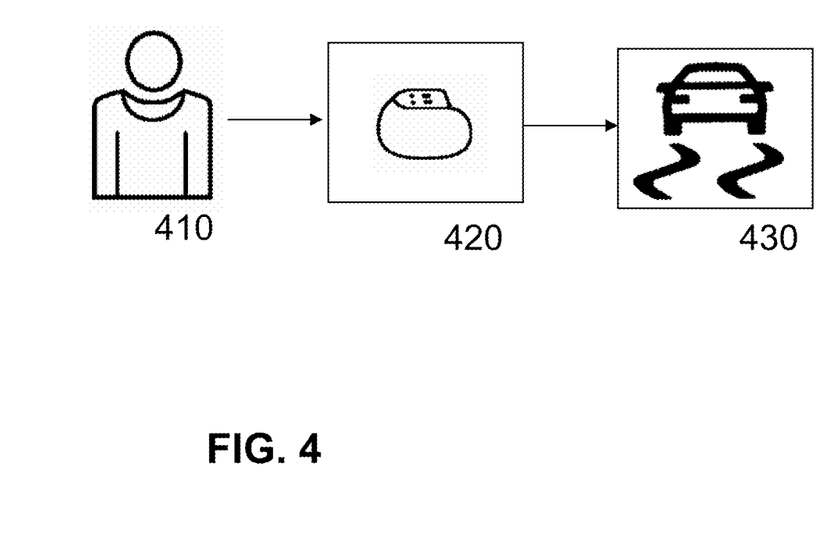
FIG. 4 is a further illustration of the prior art.

FIG. 4 illustrates the prior art once again (compare to FIG. 1). Based on physiological parameters of the patient 410, an electronic implant 420 deduces the need for making a direct intervention in the driving operations of a vehicle 430. In this case the intervention itself is always predetermined (for example, braking to a stop), and may also optionally involve feedback to the therapeutic control system of the implant. Thus, for example, it is provided that a cardioversion treatment is delayed until the vehicle comes to a stop. None of the known approaches provides for influencing the vehicle on an individual patient basis and as a function of the driving situation.

Figure 5:
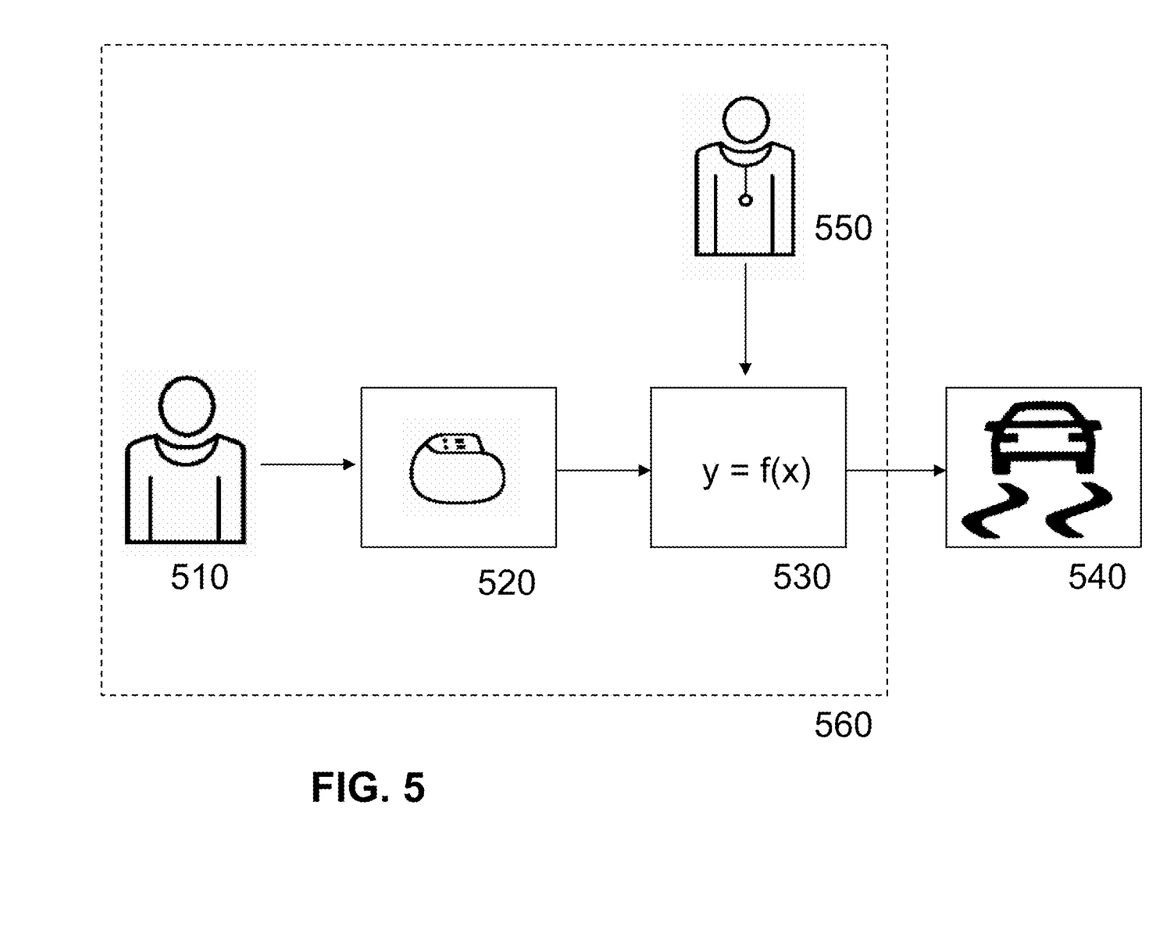
FIG. 5 is an illustration of the sequence of a driving fitness classification.

FIG. 5 illustrates the approach according to one or more embodiments of the invention. The electronic implant 520 first derives one or more physiological data items of detected parameters of the patient 510 which describe the physiological state, and signals these physiological data to a configurable classification unit 530. This classification unit 530 may, for example, be configured on an individual patient basis by a medical practitioner 550 in such a way that this classification unit 530 forms a suitability index which describes a driving fitness state of a patient as a function of the physiological data from the implant 520, and signals same to a vehicle or driver assistance system 540, i.e., a vehicle control system. The driver assistance system 540 used here forms a machine control system within the meaning of the claims, and in contrast to the prior art receives from the classification unit not a direct driving instruction, but, rather, in the form of the suitability index receives only information concerning the driving fitness state of the patient. The driver assistance system 540 then derives an appropriate influence of the driving, based on the driver fitness information and other relevant driving information (speed, distance sensors, yaw rate, etc.).

In the present case the safety system is basically divided into a medical product system 560 and the vehicle system, so that the responsibility for the description and classification of the driving fitness state lies with the medical product manufacturer and the medical practitioner, whereas the responsibility for influencing the vehicle itself lies with the vehicle manufacturers and their suppliers.

Figure 6:
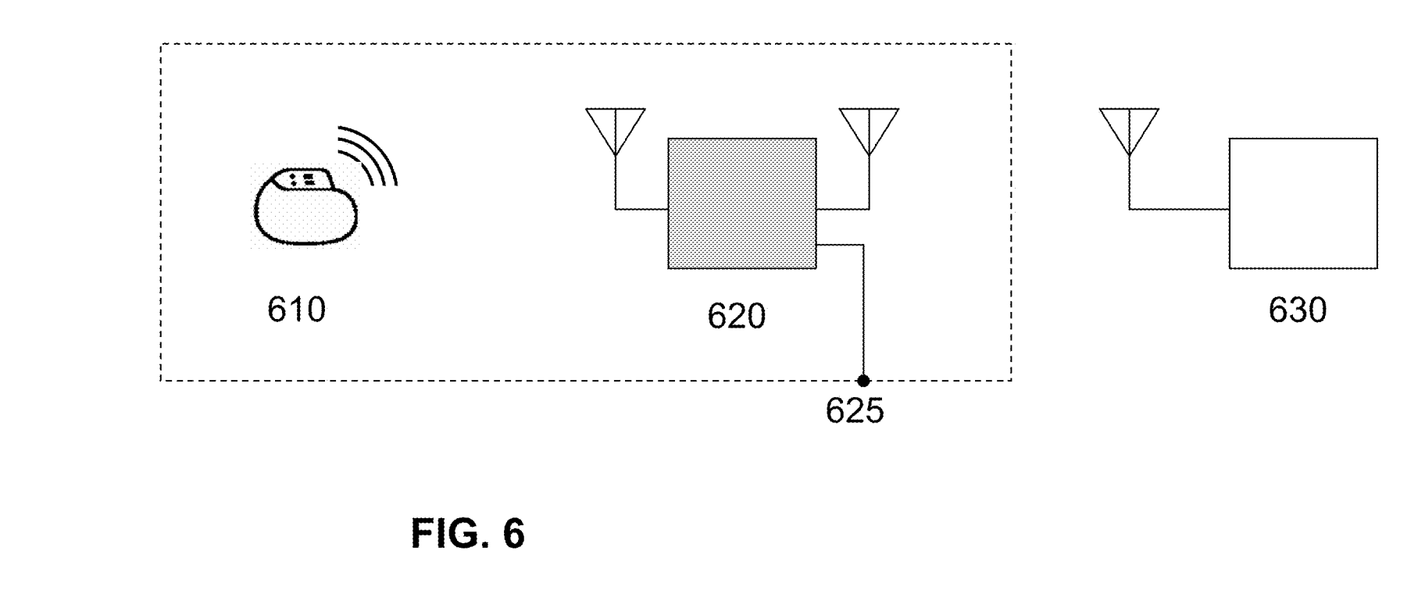
FIG. 6 shows a block diagram of a safety system according to the invention.

FIG. 6 shows a block diagram of the safety system according to the invention. The safety system includes an electronic implant 610 which, preferably in the MICS or ISM band, transmits diagnostic or therapeutic information in the form of physiological data to a classification unit 620. In this system the classification unit 620 is a component of a control device as a relay station between the implant and the vehicle, but optionally may also be a component of the electronic implant. The information from the implant may be assigned on an individual patient basis to various driving fitness descriptions via an interface 625 which is accessible to the medical practitioner. This driving fitness description is then transmitted, via an interface which is preferred in the automotive sector, to the vehicle system 630, where it may be used as additional information for driver assistance systems.

Figure 7:
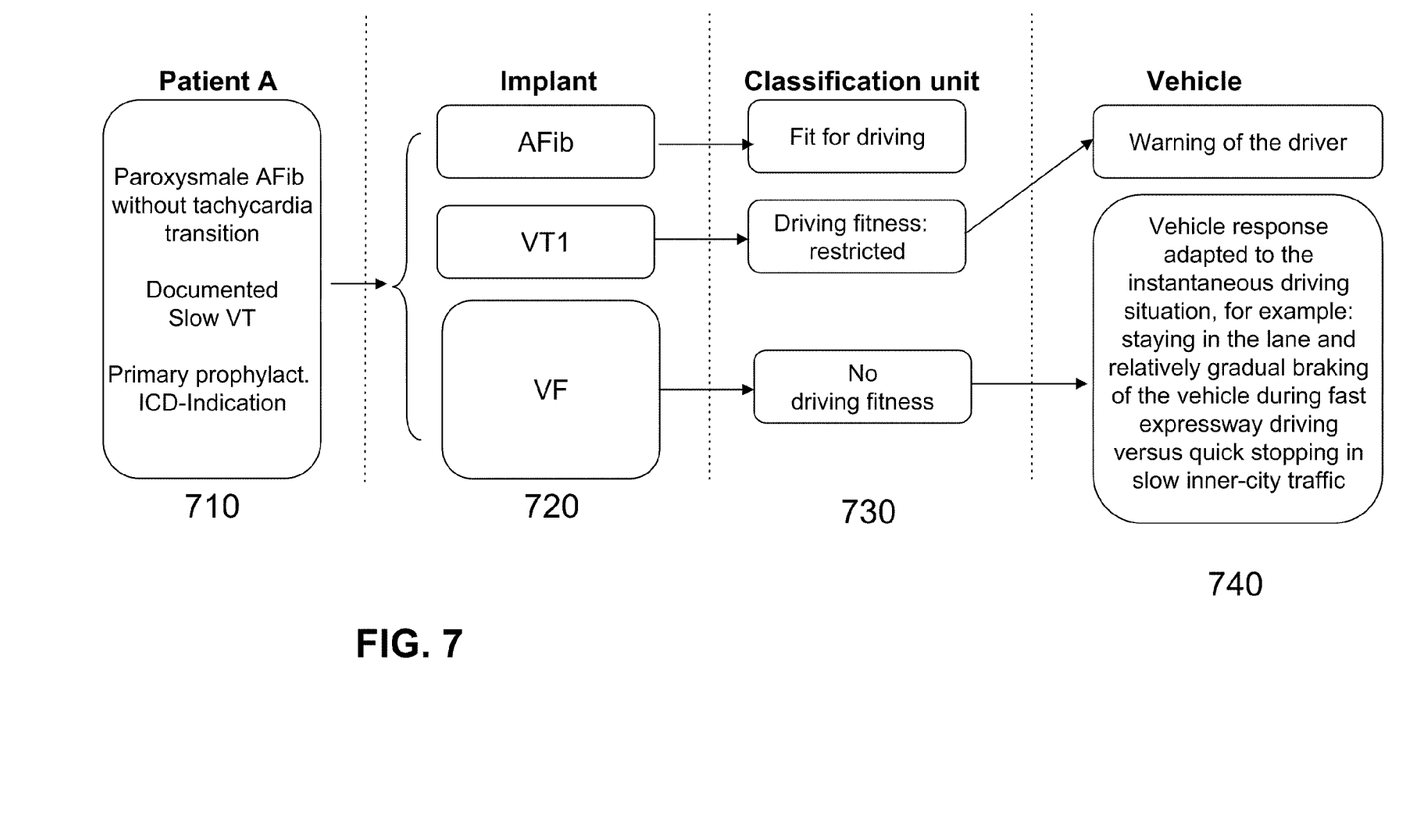
FIG. 7 shows a first example classification A.

FIG. 7 shows one possible classification individually prepared for a patient A. This patient A 710 has received a single-chamber ICD implant since he has met the criteria for primary prophylaxis. In addition, the medical practitioner is aware that the patient suffers from paroxysmal atrial fibrillation without tachycardia transition, and hemodynamic consequences. Slow ventricular tachycardia has also been documented, which over prolonged periods may cause dizziness in the patient.

The implant 720, an implantable cardioverter/defibrillator (ICD), is able to classify the cardiological states of the patient and automatically provide treatment as needed. The following are activated for this patient: a class for diagnosing atrial fibrillation (AFib), which does not result in treatment by the ICD; a class for detecting typical slow ventricular tachycardia (VT1), which includes painless ATP treatment; and a class for recognizing ventricular fibrillation (VF), using automatic defibrillation shock therapy with up to 8 shocks in succession.

The attending medical practitioner has stored the driving fitness of the patient in the classification unit 730 as follows: for atrial fibrillation the driving fitness is not restricted. For slow ventricular tachycardia the driving fitness is restricted (i.e., at least for the 10 minutes following VT detection), and driving fitness is no longer indicated for the ventricular fibrillation class.

This information concerning the driving fitness is relayed to the driver assistance system 740, which is part of a machine control system or vehicle electronics system of the vehicle. In the event of limited driving fitness, the system indicates to the driver that the vehicle must be switched off immediately, but does not actively intervene in the driving operations. In the event that driving fitness is no longer present, the driver assistance system takes control of the vehicle with the objective of safely stopping the vehicle, depending on the driving situation. However, for this purpose all other sensor information from the vehicle is included, so that the vehicle response is adapted to the instantaneous driving situation (for example, staying in the lane and relatively gradual braking of the vehicle during fast expressway driving versus quick stopping in slow inner-city traffic).

Figure 8:
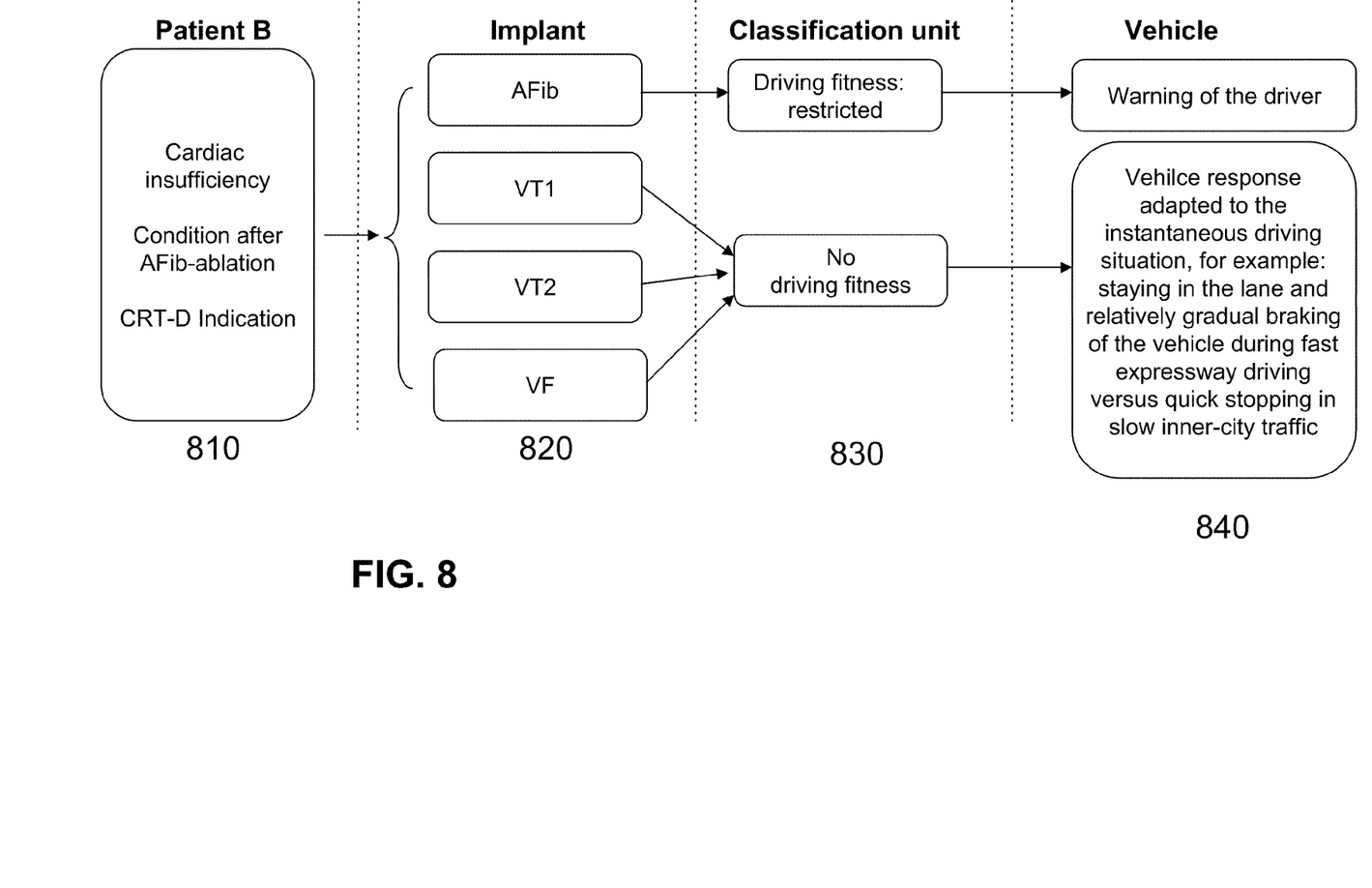
FIG. 8 shows a second example classification B as an alternative to FIG. 7.

FIG. 8 illustrates one possible classification individually prepared for a patient B. This patient B 810 has received a triple-chamber ICD (CRT-D) implant since he has met the criteria for cardiac resynchronization therapy due to pronounced cardiac insufficiency. At the same time, atrial fibrillation ablation was performed to treat atrial fibrillation with tachycardia transition.

The implant 820, an ICD, is able to classify the cardiological states of the patient and automatically provide treatment as needed. The following are activated for this patient: a class for diagnosing atrial fibrillation (AFib), which does not result in treatment by the ICD; two classes for detecting ventricular tachycardia (VT1, VT2), which include painless ATP treatment and shock therapy; and a class for recognizing ventricular fibrillation (VF), using automatic defibrillation shock therapy with up to 8 shocks in succession.

The attending medical practitioner has stored the driving fitness of the patient in the classification unit 830 as follows: for atrial fibrillation the driving fitness is conditionally restricted, since this condition may result in loss of effective resynchronization, and therefore after 15-20 minutes dizziness or momentary loss of consciousness cannot be ruled out. Driving fitness is no longer indicated for the ventricular fibrillation class.

This information concerning the driving fitness is relayed to the driver assistance system 840. In the event of limited driving fitness, the system indicates to the driver that the vehicle must be switched off immediately, but does not actively intervene in the driving operations. In the event that driving fitness is no longer present, the driver assistance system takes control of the vehicle with the objective of safely stopping the vehicle, depending on the driving situation. However, for this purpose all other sensor information from the vehicle is included, so that the vehicle response is adapted to the instantaneous driving situation (for example, staying in the lane and relatively gradual braking of the vehicle during fast expressway driving versus quick stopping in slow inner-city traffic).

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE NUMERALS

110 Implant
120 Vehicle
210 Electronic implant
220 Vehicle key
230 Vehicle
320 MICS radio band
330 Antenna
350 Antenna
340 Communication module
360 Security server
370 Maintenance interface
410 Patient
420 Implant
430 Vehicle
510 Patient
520 Implant
530 Classification unit
540 Driver assistance system
550 Medical practitioner
560 Medical product system
610 Implant
620 Classification unit
625 Interface
630 Vehicle system
710 Patient A
720 Implant
730 Classification unit
740 Driver assistance system
810 Patient B
820 Implant
830 Classification unit
840 Vehicle

What is claimed is:

1. A control device comprising:
a first interface configured to communicate wirelessly with an implant;
a second interface configured to communicate with a machine having a machine control system;
a memory for a unique identifier, wherein the first interface is configured to receive physiological data or a suitability index from said implant which describes a fitness of an implant wearer to operate the machine, and wherein the fitness of an implant wearer to operate the machine com rises at least a restricted driving fitness category, a conditionally restricted driving fitness category, and an unrestricted fitness driving category;
a classification unit configured to
store the driving fitness categories of said implant wearer to operate the machine,
receive said physiological data, in each case to assign said physiological data to one of a plurality specified suitability classes,
generate an index which denotes a particular assigned suitability class, and
provide the index as said suitability index to the second interface;
wherein the classification unit is further configured to be tailored to physiological concerns of a particular implant wearer, and to requirements imposed for said driving fitness categories to operate the machine; and,
wherein the second interface is configured to transmit the suitability index together with the unique identifier to the machine control system of the machine.

2. The control device according to claim 1, wherein the second interface configured to communicate has a short communication range of several centimeters.

3. The control device according to claim 1, wherein the second interface is configured to transmit data in the ISM (Industrial, Scientific and Medical) frequency band, with a range of 433 MHz and 2.4 GHz.

4. The control device according to claim 1, wherein the control device is configured as an electronic vehicle key.

5. A safety system comprising:
an implant;
a machine having a machine control system;
a control device comprising
a first interface configured to communicate wirelessly with said implant;
a second interface configured to communicate with said machine having said machine control system;
a memory for a unique identifier, wherein the first interface is configured to receive physiological data or a suitability index from said implant which describes a fitness of an implant wearer to operate the machine;
wherein the fitness of an implant wearer to operate the machine comprises at least a restricted driving fitness category, a conditionally restricted driving fitness category, and an unrestricted fitness driving category;
wherein the second interface is configured to transmit the suitability index together with the unique identifier to the machine control system of the machine;
wherein said machine control system which is configured to allow operation of the machine only when the unique identifier has been received, and to set an operating mode of the machine as a function of the suitability index, wherein the implant is configured to detect said physiological data of the implant wearer, and to either generate the suitability index based on said physiological data and transmit the suitability index to the control device, or to transmit the physiological data itself to the control device; and,
wherein said machine control system is further configured to indicate to the implant wearer that the machine must be switched off when a restricted driving fitness category is described in the suitability index.

6. The safety system according to claim 5, wherein the machine is a vehicle and the machine control system is part of a vehicle electronics system.

7. An implant-control system comprising:
an implant configured as a medical implant;
a control device comprising
a first interface configured to communicate wirelessly with the implant;
a second interface configured to communicate with a machine having a machine control system;

a memory for a unique identifier, wherein the first interface is configured to receive physiological data or a suitability index from said implant which describes a fitness of an implant wearer to operate the machine;

wherein the fitness of an implant wearer to operate the machine comprises at least a restricted driving fitness category, a conditionally restricted driving fitness category, and an unrestricted fitness driving category;

wherein the second interface is configured to transmit the suitability index together with the unique identifier to the machine control system of the machine;

wherein the implant is configured to detect said physiological data of the implant wearer; and, a classification unit which is configured to receive said physiological data, in each case to assign said physiological data to one of a plurality of specified suitability classes, and to generate the suitability index which denotes a particular assigned suitability class.

8. The implant-control system according to claim 7 wherein:

the control device comprises said classification unit;

said implant is configured to transmit the physiological data to the control device, said classification unit is configured to provide the suitability index to the second interface.

9. The implant-control system according to claim 7 wherein:

said classification unit is configured to transmit the suitability index to the control device;

the control device configured to provide a particular suitability index, received from the implant, to the second interface.

10. The implant-control system according to claim 7, wherein the implant is a cardiac stimulator.

11. A method for controlling a machine, comprising:

generating physiological parameters which describe physiological data from an implant;

forming a suitability index from the physiological data; and, transmitting the suitability index together with a unique identifier from a control device comprising a first interface configured to communicate wirelessly with the implant;

a second interface configured to communicate with a machine having a machine control system;

a memory for the unique identifier, wherein the first interface is configured to receive said physiological data or said suitability index from said implant which describes a fitness of an implant wearer to operate the machine, and wherein the fitness of an implant wearer to operate the machine comprises at least a restricted driving fitness category, a conditionally restricted driving fitness category, and an unrestricted fitness driving category; and to said machine comprising said machine control system.

12. The method according to claim 11, further comprising: controlling the machine as a function of the suitability index received by the machine control system.

13. The safety system according to claim 5, wherein the control device further comprises a classification unit configured to store the driving fitness categories of said implant wearer to operate the machine, receive said physiological data, in each case to assign said physiological data to one of a plurality of specified suitability classes, generate an index which denotes a particular assigned suitability class, and provide the index as said suitability index to the second interface; and, wherein the classification unit is further configured to be tailored to physiological concerns of a particular implant wearer, and to requirements imposed for said driving fitness categories to operate the machine.

14. The implant control system according to claim 7, wherein the classification unit is further configured to be tailored to physiological concerns of a particular implant wearer, and to requirements imposed for said driving fitness categories to operate the machine.

15. The method for controlling a machine according to claim 11, wherein the control device further comprises a classification unit configured to store the driving fitness categories of said implant wearer to operate the machine, receive said physiological data, in each case to assign said physiological data to one of a plurality of specified suitability classes, generate an index which denotes a particular assigned suitability class, and provide the index as said suitability index to the second interface; and, wherein the classification unit is further configured to be tailored to physiological concerns of a particular implant wearer, and to requirements imposed for said driving fitness categories to operate the machine.

* * * * *